United States Patent [19]

Lange

[11] Patent Number: 4,707,301

[45] Date of Patent: Nov. 17, 1987

[54] NORBORNYL DIMER ESTER AND POLYESTER ADDITIVES FOR LUBRICANTS AND FUELS

[75] Inventor: Richard M. Lange, Euclid, Ohio

[73] Assignee: The Lubrizol Corporation, Wickliffe, Ohio

[21] Appl. No.: 884,573

[22] Filed: Jul. 11, 1986

[51] Int. Cl.[4] .............. C10M 137/10; C10M 153/04
[52] U.S. Cl. ..................... 252/46.6; 252/49.3; 558/156
[58] Field of Search .............. 558/156; 252/46.6, 49.3

[56] References Cited

U.S. PATENT DOCUMENTS

| | | | |
|---|---|---|---|
| 2,644,002 | 6/1953 | Hoegberg | 260/326.5 |
| 3,023,209 | 2/1962 | Reese et al. | 260/250 |
| 3,401,175 | 9/1968 | Osborne et al. | 260/326 |
| 3,849,473 | 11/1974 | Inamoto et al. | 260/468 G |
| 3,962,105 | 6/1976 | Lange | 252/56 R |
| 4,002,568 | 1/1977 | Jayne et al. | 252/46.6 |
| 4,028,258 | 6/1977 | Kablaoui | 252/46.7 |
| 4,306,984 | 12/1981 | Yamaguchi | 252/46.7 |

*Primary Examiner*—William R. Dixon, Jr.
*Assistant Examiner*—Ellen McAvoy
*Attorney, Agent, or Firm*—Denis A. Polyn; Forrest L. Collins; Karl Bozicevic

[57] ABSTRACT

Novel dimer esters and polyesters derived from and adduct of 5-norbornene-2,3-dicarboxylic anhydride and O,O-dialkyldithiophosphoric acid have been produced. These dimer esters and polyesters are useful extreme pressure agents, antiwear agents and oxidation inhibitors as well as friction modifying agents for functional fluids used in motorized vehicles.

21 Claims, No Drawings

NORBORNYL DIMER ESTER AND POLYESTER ADDITIVES FOR LUBRICANTS AND FUELS

BACKGROUND OF THE INVENTION

1. Field of the Invention

This invention relates to novel norbornyl dimer ester and polyester additives for functional fluids. It has been discovered that these additives improve the extreme pressure, antiwear, antioxidant and friction modifying properties of functional fluids, e.g., lubricants, and fuels for use in internal combustion engines and the machinery of motorized vehicles.

2. State of the Art

Monomeric norbornyl ester adducts of O,O-dialkyl-dithiophosphoric acid have been disclosed in the art. For example, in U.S. Pat. No. 3,023,209, various dialkyl-dithiophosphoric acid esters of norbornene reactants are disclosed as possessing good insecticidal, fungicidal and miticidal properties. It is also disclosed that these compounds have properties rendering them useful as corrosion inhibitors, plasticizing agents, lubricating oil additives and flotation agents, etc.

U.S. Pat. No. 3,962,105 discloses various diesters and/or ester lactones of norbornene systems which are useful as seal swell additives.

In U.S. Pat. No. 4,028,258, a transmission fluid is disclosed comprising an alkylene oxide adduct of a phosphosulfurized N-(hydroxyalkyl) alkenyl succinimide.

Insecticidal alkoxy and haloalkoxyphenol-phosphinyloxy and phosphinothioloxy-1,3-isoindoledones are disclosed in U.S. Pat. No. 3,401,175.

In U.S. Pat. No. 2,644,002, dialkyldithio-phosphoric acid esters of succinimides are disclosed as being adaptable for various uses such as insecticides, fungicides, plasticizers, corrosion inhibitors, flotation agents, and petroleum additives.

Diesters of 1,3-bis(carboxymethyl) adamantanes which are useful as oiling agents for synthetic fibers and as synthetic lubricating oil bases are disclosed in U.S. Pat. No. 3,849,473.

None of the foregoing disclosures teach the norbornyl dialkyldithiophosphoric acid adduct, dimer ester or polyester products of the present invention. Futhermore, there is no disclosure of such products utilized as extreme pressure agents, and antiwear agents or friction modifying agents for functional fluids to be used in internal combustion engines and the machinery of a motorized vehicle.

SUMMARY OF THE INVENTION

In accordance with the present invention novel dimer ester and polyester materials derived from adducts of O,O-dialkyldithiphosphoric acids and 5-norbornene-2,3-dicarboxylic anhydride have been discovered.

Further, in accordance with the present invention functional fluids, e.g., lubricants and fuels comprising a friction modifying, extreme pressure and/or antiwear effective amount of the dimer or polymer products of the present invention are provided.

Still further in accordance with the invention, additives and concentrates comprising a diluent/solvent and one or more of the norbornyl containing reaction products of the present invention are provided for formulating with functional fluids.

Still further in accordance with the present invention, a method for improving the load bearing characteristics and fuel economy properties of functional fluids used in motorized vehicles is provided.

These and other aspects of the invention will become clear to those skilled in the art upon the reading and understanding of the specification.

DETAILED DESCRIPTION OF THE INVENTION

The norbornyl dimer ester adducts of the present invention may be represented by the following formula I:

$$A-T-A \qquad (I)$$

wherein A is

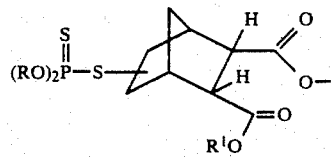

where R is alkyl, aryl or aralkyl and $R^1$ is, independently, hydrogen or hydrocarbyl and T is hydrocarbyl.

The norbornyl polyester adduct according to the present invention may be represented by the formula II:

wherein X and Y are terminal groups of the polymer and are, independently, hydrogen, alkyl, aryl, aralkyl, hydroxy, alkoxy, carboalkoxy, aryloxy, dialkylamino, diarylamino, alkylthio or arylthio; p is 3 to about 30; r is 0 to about 30 and the sum of p+r ranges from 3 to about 40; D is

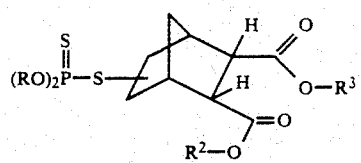

wherein R is alkyl, aryl or aralkyl and $R^2$ and $R^3$ are a bond to other repeating units; and E is

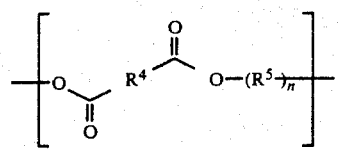

wherein $R^4$ and $R^5$ are the same or different and are hydrocarbyl which includes branched hydrocarbyl groups containing reactive functionalities thereof, and n is 0 or 1.

For the purposes of the present invention, formula (II) is intended to random and alternating polymers, as well as block and graft copolymers. In the event formula (II) represents a block copolymer, the respective homogeneous blocks of repeating D and E segments may each comprise random or alternating sequences within each of these segments.

As used herein, the terms "hydrocarbyl" or "hydrocarbon-based" denote a radical having a carbon atom directly attached to the remainder of the molecule and having predominantly hydrocarbon character within the context of this invention. Such radicals include the following:

(1) Hydrocarbon radicals; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical). Such radicals are known to those skilled in the art; examples include methyl, ethyl, butyl, hexyl, octyl, decyl, dodecyl, tetradecyl, octadecyl, eicosyl, cyclohexyl, phenyl and naphthyl (all isomers being included).

(2) substituted hydrocarbon radicals; that is, radicals containing non-hydrocarbon substituents which, in the context of this invention, do not alter the predominantly hydrocarbon character of the radical. Those skilled in the art will be aware of suitable substituents (e.g., halo, hydroxy, alkoxy, carbalkoxy, nitro, alkylsulfoxy).

(3) Hetero radicals; that is, radicals which, while predominantly hydrocarbon in character within the context of this invention, contain atoms other than carbon atoms. Suitable hetero atoms will be apparent to those skilled in the art and include, for example, nitrogen, oxygen, phosphorus and sulfur.

Terms such as "alkyl-based radical", "aryl-based radical" and the like have meaning analogous to the above with respect to alkyl and aryl radicals and the like.

The radicals are usually hydrocarbon and especially lower hydrocarbon, the word "lower" denoting radicals containing up to seven carbon atoms. They are preferably lower alkyl or aryl radicals, most often alkyl.

The preparation of the norbornene starting material used to react with the dialkyldithiophosphoric acid, i.e., 5-norbornene-2,3-dicarboxylic anhydride is described in Onishchenko, *Diene Synthesis* (translation from the Russian by Isreal Program for Scientific Translations, Jerusalem, 1964), Daniel Davey and Company, Publisher, New York (1964), pages 38, 47, 48–50. In general, the preparation of this reaction product involves the reaction of dicyclopentadiene with maleic anhydride to produce the desired 5-norbornene-2,3-dicarboxylic anhydride.

The above norbornene dicarboxylic anhydride reactant is then reacted with a dialkyldithiophosphoric acid of the formula:

(RO)$_2$P(S)SH to form the norbornyl dialkydithiophosphate intermediate anhydride. This material may be represented by the following formula:

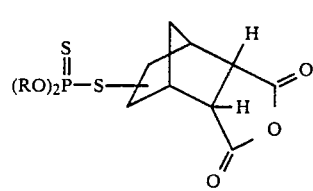

The alkyl, aryl or aralkyl group R of the phosphoric acid may contain 1 to about 30 carbon atoms and preferably 3 to about 12 carbon atoms. The R group may be the same or different dependent upon the properties desired to impart to the particular functional fluid, e.g., oil solubility, antiwear and the like. Also, the anhydride group on the norbornyl ring may be in the endo or exo position or there may be mixtures of these isomers.

The above compound (represented by formula III) is further reacted with other reagents in order to produce the dimer ester (I) or polyester (II) products.

The dimer esters of (I) may be prepared by condensing the anhydride adduct (III) with diols (or polyols), or with mixtures of diols (or polyols) and monoalcohols, in ratios such that the products are dimeric. For example, with a glycol, HO—R$^2$—OH, (III) gives

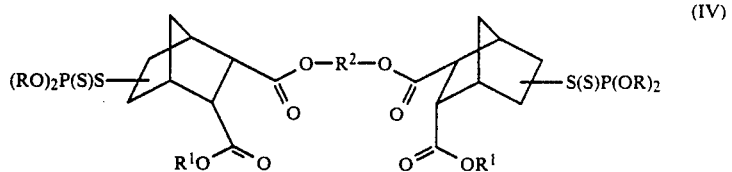

wherein R$^1$ is H or hydrocarbyl, i.e., a primary or secondary C$_2$ to C$_{200}$ alkyl, aralkyl, aryl or alkylaryl (linear or branched), and may contain unsaturation, halogen or heteroatoms, alicyclic or heterocyclic rings, fused rings. It may also have pendant or incorporated functionality such as —OH, —NR$_2$, carbonyl in a diversity of structures (ester, carboxylic acid, aldehyde, ketone, amide or imide), corresponding thio-carbonyl moieties (thioesters, thiolesters, dithioesters, thio- and dithiocarbamates), halogen, alkoxy, alkylthio, mercapto, phosphate, phosphite, phosphonate, dithiophosphate and/or phosphoramide moieties and wherein R$^2$ is C$_2$ to C$_{200}$ alkylene or arylene (linear or cyclic in structure), having optionally one or more heteroatoms such as halogen, O, S, or N which can also contain one or more polar functions including those described for R$^1$ above.

Furthermore, R$^2$ may be polymeric in nature, derived from ring-opening reactions of epoxides, lactones or lactams, or through condensation reactions of diols or aminoalcohol with lactones, lactams, epoxides, and/or dicarboxylic acids (or their esters).

Other useful polymeric R$^2$ radicals may be derived from other such hydroxy-containing polymers as sugars, starches, alkyl alcohol copolymers, polyvinyl alcohol and partially-hydrolyzed polyvinyl carboxylates.

When R$^1$ is H, dimer IV may be converted to salts of metals selected from Group IA and IIA of the periodic table, as well as from the various transition metals which include Zn, Cd, Sn, Pb, Sb, Cu, Ni, Mn, Co, Fe, Ce, Ti, Zr, the lanthanides, and the complex uranyl cation, UO$_2^{+2}$.

The salts of adduct (IV) may be made more soluble in oil or in aqueous solution by using appropriate alkyl (R)

groups, and by amine complexation, where this is feasible (as with transition metal ions).

The polymeric derivatives of adduct (III) may be prepared by the condensation of diols (and/or polyols) with adduct (III) to produce the polymeric derivative represented by (II). The condensation reaction is carried out such that equivalent ratios of OH:C=O (or more usually, with reatios having 1 to 10% excess OH) are used, and the reaction is carried out to the point of complete removal of water. The products are of molecular weights of about 1000 to about 10,000 (usually 1000 to 3000), and are oil-soluble due to the size and nature of the R group in the dithiophosphate ester portion of the molecule.

The polymeric derivatives (II) may be more specifically illustrated by the following formula:

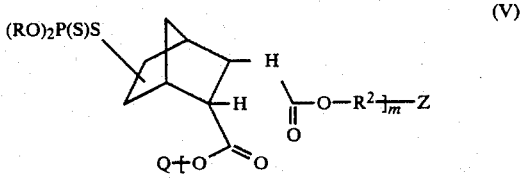

(V)

where Q is H, $C_1$ to $C_{30}$ alkyl or aryl (or OH-containing alkyl or aralkyl), which also may contain heteroatoms (e.g., O, S, N, P, halogen or other functionality); Z is —OH, $C_1$ to $C_{30}$ alkoxy, carbalkoxy or aryloxy, which groups may also contain heteroatoms (S, O, N), dialkyl (or diaryl)-amino, or alkylthio, or arylthio, halogen as well as other functionalities; m is 3 to 30; preferably 4 to 10, and $R^2$ is the same as described for IV above.

Moreover, di- and/or polycarboxylic acids may be co-condensed with compound (III) and reactive diols (or polyols). Of particular interest are those acids which are used in the production of other linear or branched (e.g., alkyd) resins, among which are:

(a) alkyl and alkenyl succinic acids (or the corresponding anhydrides);

(b) $C_4$ to $C_{20}$ alpha-omega-dicarboxylic acids (e.g., succinic, glutaric, adipic, azaleic);

(c) the so-called "dimer acids," made by Emery Corp. from vegetable acids, and containing approximately 36 carbon atoms;

(d) the isomeric phthalic acids (in particular isophthalic and terephthalic);

(e) maleic, itaconic, citraconic, tricarballylic;

(f) pyromellitic, trimellitic;

(g) tartaric, citric, lactic;

(h) maleinated $C_{11}$ to $C_{18}$ fatty acids;

(i) Diels-Alder adducts of 1,3-dienes, such as 1,3-butadiene, cyclopentadiene, 1,3-cyclohexadiene, 1,3-cyclooctadiene, 1,3-cyclododecandiene or isoprene with alpha,beta-unsaturated dicarboxylic acids; and (j) heteroatom-coupled carboxylic acids, such as thiodiacetic, thiopropionic, iminodiacetic, nitroacetic and the like.

The resulting co-condensation products are mixed linear and/or branched polyesters of general structure (VI), which exhibit remarkable load-bearing (EP) and antiwear properties in lubricating oil compositions as well as friction modifying and dispersancy properties.

These polyester products may be represented more specifically by the following formula VI which is encompassed by (II).

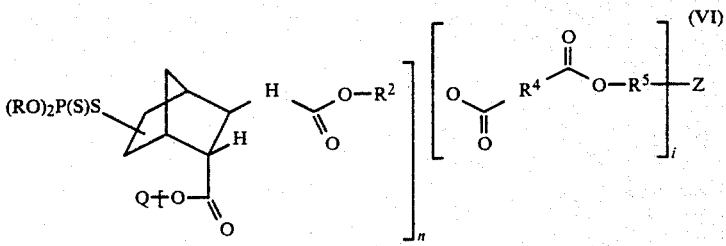

wherein Q and Z are the same as defined in (V) above; where the sum of n and i is preferably 3 to 30 and most preferably 4 to 10. $R^2$ is the same as defined in (IV) above and $R^4$ is $C_2$ to $C_{20}$ alkylene, aralkylene or cycloalkylene, $C_6$ to $C_{30}$ arylene or akylarylene [with or without heteroatoms, halogen, or other functionality (e.g., carboxylic acid, ester, amide or imide, ketone, aldehyde), hydroxy, alkoxy, alkylthio, carbalkoxy, etc.]

In a preferred embodiment of this invention, $R^4$ is derived from a $C_{10}$ to $C_{100}$ alkenylsuccinic anhydride prepared from a $C_8$ to $C_{98}$ olefin or polyolefin and maleic anhydride at 200°-230° C. in an Alder (or "Ene") condensation. In this instance, oil-solubility and performance properties of structure (VI) is dependent on the nature of R in the dithiophosphate portion of the adduct and the pendant hydrocarbon tail of the alkenylsuccinic acid portion of the polyester.

With respect to different polyol and mono- or polycarboxylic acid reactants that may condensed with adduct (III), the selection of the specific polyol or mono- and/or polyacid is dependent upon the properties desired for the end product as well as such pragmatic considerations as cost. Representative of diols useful in the practice of this invention are typically dihydric alcohols or functional derivatives thereof, such as esters, which are capable of condensing with diacids or their functional derivatives to form condensation polymers. These diols can be represented, for example, by the formula $R^6O$—$R^2$—$OR^6$ wherein each $R^6$ is hydrogen or alkylcarbonyl, preferably of from 2 to 7 carbon atoms. An alkylcarbonyl can be represented by the formula

wherein $R^7$ is alkyl preferably of from 1 to 6 carbon atoms. Representative alkylcarbonyl radicals are acetyl, propionyl, butyryl, etc. More preferably, each $R^6$ is hydrogen.

$R^2$ is an aliphatic, alicyclic or aromatic radical, preferably of 2 to 12 carbon atoms, more preferably of 2 to 6 carbon atoms and, optionally, including, oxygen and/or sulfur atoms. Typical aliphatic, alicyclic and aromatic radicals include alkylene, cycloalkylene, alkylidene, arylene, alkylidyne, alkylenearylene, alkylenecycloalkylene, alkylenebisarylene, cycloalkylenebisalkylene, arylenebisalkylene, alkylene-oxy-alkylene, alkylene-oxy-arylene-oxyalkylene, etc. Preferably, $R^2$ is hydrocarbon, such as alkylene, cycloalkylene, cycloalkylenebisalkylene or arylene but may also contain heteroatoms such as S, N, O, and/or P.

Exemplary diols and polyols that may be mentioned include the aliphatic polyoxyalkylene glycols, polyethylene glycol, polypropylene gylcol, polyethylene and polypropylene glycol mixtures, diethylene glycol, thiethylene glycol, tetraethylene glycol, pentaethylene glycol, hexaethylene glycol, heptaethylene glycol, oxyethylene glycol, dipropylene glycol, and mixtures thereof. Preferably the polyoxyalkylene glycol is selected from the group consisting of diethylene glycol, triethylene glycol, and mixtures thereof. Also included are thiodiethanol, dithiodiethanol, di(2-hydroxyethyl)amides and the like.

Other diols useful in the preparation of polymers of the invention also include non-oxyalkylated aliphatic, cycloaliphatic and aromatic glycols. Representative examples include propylene glycol, 1,3-propane diol, neopentyl glycol, 1,3-butane diol, 1,5-pentane diol, 1,6-hexane diol, catechol, resorcinol, and hydroquinone. Preferred diols of this class are selected from the group consisting of ethylene glycol, propylene glycol and 1,4-butane diol.

The representative carboxylic acids useful for the present invention include any suitable polycarboxylic acid such as oxalic acid, malonic acid, succinic acid, glutaric acid, adipic acid, pimelic acid, suberic acid, azelaic acid, sebacic acid, maleic acid, fumaric acid, glutaconic acid, alpha-hydromuconic acid, beta-hydromuconic acid, alpha-butyl-alpha-ethyl-glutaric acid, alpha,beta-diethylsuccinic acid and 1,4-cyclohexane-dicarboxylic acid, 4-cyclohexane-1,2-dicarboxylic acid, 2-ethylsuberic acid, 2,2,3,3-tetramethylsuccinic acid, 4,4'-bicyclohexyldicarboxylic acid, diglycolic, thiodipropionic, and other similar acids including those disclosed, for example, in U.S. Pat. Nos. 3,546,180; 3,929,489; and 4,101,326. Alkyl ester, acid halide and anhydride derivatives of these acids are also useful in the practice of this invention.

Representative unsaturated dicarboxylic acid reactants include aromatic acids including phthalic, terephthalic, isophthalic, 2,5-norbornane dicarboxylic, 1,4-naphthalic, diphenic, 4,4-oxydibenzoic, 4,4'-sulfonyldibenzoic, and 2,5-naphthalene dicarboxylic acids.

Representative polyfunctional reactants are trimesic acid, trimellitic acid, trimellitic anhydride, pyromollitic acid, butanetetracarboxylic acid, naphthalenetricarboxylic acids, cyclohexane-1,3,5-tricarboxylic acid, glycerol, trimethylolpropane, pentaerythritol, dipentaerthritol, 1,2,6-hexanetroil, 1,3,5-trimethylolbenzene, malic acid, citric acid, 3-hydroxyglutaric acid, 4-beta-hydroxyethylphthalic acid, 2,2-dihydroxymethylpropionic acid, 10,11-dihydroxyundecanoic acid, 5-(2-hydroxyethoxy)isophthalic acid and others known in the art as disclosed, for example, in U.S. Pat. No. 4,013,624.

The dimer esters and polyesters of this invention can be prepared by standard procedures. Typically, such procedures involve the reaction of the dicarboxylic acids (or diesters, anhydrides, etc., thereof) with polyhydric alcohols in the presence of an acid catalyst, such as an aryl sulfonic acid or alkyl sulfonic acid, or an organic titanate, such as tetrabutyl titanate, utilizing heat and reduced pressure as desired. Normally, an excess of the volatile polyhydric alcohol is supplied and removed by conventional techniques in the latter stages of polymerization. To protect the polyester from oxidation, an antioxidant such as a hindered phenol can be added to the reaction mixture.

In general, the dimer ester and polyester products of the present invention may be described as the reaction product of (A) 5-norbornene-2,3-dicarboxylic anhydrides;
(B) O,O-dialkyldithiophosphoric acid; and
(C) at least one diol and/or polyol and, optionally, at least one mono-, di- or polycarboxylic acid.

The preparation of various dimer ester and polyester species within the scope of the present invention is illustrated in the following examples. While these examples will show one skilled in the art how to operate within the scope of this invention, they are not to serve as a limitation on the scope of the invention where such scope is defined only in the claims. It is pointed out that in the following examples, all percentages and all parts are intended to express percent by weight and parts by weight unless otherwise clearly indicated.

EXAMPLE 1

Preparation of Adduct of Di-isooctyl dithiophosphoric Acid and 5-Norbornene-2,3-dicarboxylic Anhydride A reaction flask was charged with 911 grams of 5-norbornene-2,3-dicarboxylic anhydride and 750 ml of toluene, heated to 70° C. to effect dissolution. After purging the system with inert nitrogen gas, 1980 grams of O,O-di-isooctyl dithiophosphoric acid was added in a continuous manner at 80°–90° C. over a period of 2 hours. The homogeneous solution was held at 90° C. for an additional 5 hours with stirring under a low nitrogen sparge, during which time the strong acid number (bromphenol blue indicator) of the reaction mixture decreased rapidly.

The solution was then vacuum-stripped at 90°–100° C. 5 torr, and filtered through a thin pad of diatomaceous earth to give 2723 grams (94% yield) of clear amber adduct (Structure III; R=isooctyl) having a bromphenol blue acid number of 2.6. The infrared specturm of the liquid showed absorptions at 1775 and 1850 cm$^{-1}$, indicative of 5-membered cyclic anhydride. Analysis: %S=11.4; %N=5.96.

EXAMPLE 2

Polyester from Ethylene Glycol

A reaction flask was charged with 560 grams of the anhydride product of Example 1, 75 grams of ethylene glycol, 300 grams of toluene and 2 grams of p-toluenesulfonic acid, and heated to reflux under a gentle sparge of nitrogen. Water of condensation was removed ocer a 10-hour period by azeotropic distillation, then the solution was cooled and washed twice with 500-ml portions of water, and stripped to 120° C./10 torr. Filtration through diatomaceous earth gave a viscous amber oil, a polyester containing 10.5% sulfur, and having an acid number (phenolpthalein indicator) of 28.

EXAMPLE 3

Polyester from Ethylene Glycol and $C_{18}$-$C_{24}$ Alkenylsuccinic Anhydride

The reaction container was charged with 560 g of the product of Example 1, 136 g of ethylene glycol and 414 g of a $C_{18}$–$C_{24}$ alkenylated succinic anhydride. This mixture was stirred and 1.9 g of p-toluenesulfonic acid catalyst was added to the mixture. The reaction mixture was further heated. At 110° C., 500 ml foluene was added to the reaction. The temperature was kept high enough to maintain a reflux. Water was removed by azeotropic distillation. After approximately 5 hrs., 16 ml water had been removed and the reaction was cooled overnight. The reaction was reheated to reflux for 6 hrs. The reaction mixture was stripped at 120° C./10 mm Hg. The product was then filtered through a cloth pad and diatomaceous earth filter aid.

EXAMPLE 4

Polyester/Urethane from Ethylene Glycol and Toluenediisocyanate

A reaction flask was charged with 489 grams of the product of Example 1, 400 ml of toluene, 160 grams of ethylene glycol and 1.5 gram of p-toluenesulfonic acid. The reaction mixture was stirred and heated to gentle reflux under a slow nitrogen sparge, and water of condensation (17 ml; 100% of theory for formation of diester) was removed over a period of 8 hr. The reaction mixture was cooled to room temperature, washed with two 500-ml portions of water, then stripped to 110° C./15 torr. Filtration through diatomaceous earth gave 590 grams of bis-(2-hydroxyethyl) ester of the product of Example 1, as a clear yellow, viscous oil containing 10.00%S and having an acid number (phenolphthalein indicator) of 10.

A mixture of 340 grams of this bis-(2-hydroxyethyl) ester and 400 ml of oil contained in a resin flask is stirred rapidly while 87 grams of toluenediisocyante is added rapidly. After the addition of 3 grams of tributylamine, the mixture is heated to 100° C. for 2 hr, during which time 300 ml of oil is added to ensure a manageable product viscosity. The mixture is then heated to 125° C., and held at that temperature for 3 hr. Condensation is followed by monotiring the infrared absorption of —NCO at 2240 cm$^{-1}$.

Filtration through a cloth pad gives a viscous oil solution of polyester/urethane product.

EXAMPLE 5

Polyester Derived from Ethylene Glycol and $C_{15}$–$C_{18}$ Alkenylsuccinic Anhydride A reaction flask was charged with 124 grams of $C_{15}$–$C_{18}$ alkenylsuccinic anhydride, 228 grams of the product of Example 1, 54 grams of ethylene glycol, 1.5 grams of p-toluenesulfonic acid and 400 ml of toluene. The mixture was heated to reflux with stirring under a gentle nitrogen sparge, and maintained at that temperature for 22 hr. to assure complete removal of water be azeotropic distillation. After cooling, the solution was washed with two 500-ml portions of water, and stripped to 110° C./torr. Filtration through diatomaceous earth gave 289 grams of viscous amber oil, containing 6.79% sulfur.

EXAMPLE 6 bis-Half Acid Ester from Pentaerythritol

A reaction mixture consisting of 1140 grams of the anhydride product of Example 1, 136 grams of monopenterythritol and 300 ml of toleune was stirred rapidly under nitrogen at 100 C. for one hour. The temperature was slowly increased go 120 C. for two hours. The solution was stripped to 120 C./20 torr, then filtered through diatomaceous earth to give 1006 grams of visous yellow oil, containing 10.3% sulfur, and having an acid number (phenolphthalein indicator) of 90. The product demonstrated ecellent solubility in oil at both 1% and 10% concentration.

The dimer and polymer materials of the present invention have been found to be useful extreme pressure agents and have been found to be useful extreme pressure agents and antiwear agents as well as friction-modifying agents.

The materials of the invention may be formulated into a functional fluid e.g., crankcase oil, automatic transmission fluid, hydraulic fluid, and the like by blending with the particular oil or functional fluid to be formulated.

The lubricating oil or other functional fluid may also be formulated with compounds of the present invention in the form of a concentrate. Such a concentrate may be prepared by adding 1% to about 99% by weight of at least 1 dimer or polymer of the present invention to a substantially inert, normally liquid organic diluent or solvent such as benzene, toluene, xylene, petroleum naphtha, mineral oil, ethylene-glycol-mono-alkylether or the like.

The amount of these additives fromulated with a particular lubricant may vary over a wide range and must be an amount to effectively impart extreme pressure antiwear, and friction modifying properties in the lubricatn. As a preferred amount, the additive may range from 0.01 weight percent to about 10 weight percent of the formulated lubricant.

The dimer and polymer materials of the present invention formulated with the particular functional fluid may contain other additives and chemistries such as dispersants, antioxidants, and the like. Such other additives and chemistries include, for example, detergents and dispersants of the ash-producing or ashless type, corrosion- and oxidation-inhibiting agents, pour point-depressing agents, auxiliary extreme pressure agents, color stabilizers and anti-foam agents. These other additives and chemistries are fully described and disclosed in U.S. Pat. No. 3,541,012; U.S. Pat. No. 3,697,428; and U.S. Pat. No. 4,234,435. The disclosures of these patents relating to such other additives and chemistries are hereby incorporated by reference for such disclosures.

A preferred dispersant according to the present invention is at least one substituted succinic acid or derivative thereof consisting of substituent groups wherein the substituent groups are derived from polyalkylene, said polyalkylene being characterized by a Mn value of 500 to about 10,000 and a Mw/Mn value of 1.0 to about 4.0.

It has also been found that the additive compounds of the present invention are useful in formulating various grease compositions. The norbornene dimer and polymer additives of the present invention are useful in both mineral and synthetic lubricating oils and greases. Synthetic oils include polyolefin oils (e.g., polybutene oil, decene oilgomer, and the like) synthetic esters (e.g., dinonyl sebacate, trioctanoic acid ester of trimethyolpropane, and the like), polyglycol oils, and the like. Greases are made from these oils by adding a thickening agent such as sodium, calcium, lithium, or aluminum salts of fatty acids such as stearic acid. These and similar thickening agents are described in U.S. Pat. Nos. 2,197,263; 2,564,561 and 2,999,066. The oils and greases of the present invention are prepared by blending an amount of the norbornene dimer or polymer additive of the present invention sufficient to impart extreme pressure properties, antiwear properties and/or friction modifying properties into the oil or grease. A useful concentration may range from about 0.1 to about 5 weight percent.

To further illustrate various functional fluid compositions, specifically lubricant compositions, comprising the compositions of the present invention, the following illustrative examples are provided. It is again pointed out that the following examples are provided for illustrative purposes only and are not to place any limitation on the scope of the invention where such scope is set out only in the claims. All parts and percentages are by weight.

Typical compositions according to this invention are listed in the following table.

TABLE I

| COMPONENTS | A | B | C | D | E | F |
|---|---|---|---|---|---|---|
| Base Oil | 90.37 | 90.87 | 92.82 | 95.0 | 81.13 | 83.18 |
| Product of Example 2 | | | | | | 2.00 |
| Product of Example 3 | 0.11 | 0.11 | 3.86 | 2.50 | | |
| Product of Example 4 | | | | | 2.60 | |
| Reaction Product of Polybutenyl Succinic Anhydride with Ethylene Polyamine | | | | | 3.61 | 2.50 |
| Reaction Product of Polybutenyl Succinic Anhydride with Ethylene Polyamine and Pentaerythritol | | | | | 2.50 | |
| Reaction Product of Polybutenyl Succinic Anhydride with Ethylene Polyamine and Carbon Disulfide | 2.00 | 2.00 | | | | |
| Reaction Product of Polybutenyl Succinic Anhydride with Ethylene Polyamine and Boric Acid | 1.00 | 1.00 | | | | |
| Basic Calcium Alkylbenzene-sulfonate | 1.79 | 1.79 | | | 1.10 | |
| Basic Magnesium Alkylbenzene-sulfonate | | | | | 1.35 | 0.65 |
| Reaction Product of Maleic Anhydride-styrene Copolymer with Alcohol and Amine | 3.50 | 3.50 | 1.11 | 0.20 | | |
| Hydrogenated Styrene-diene Block Copolymer Viscosity Improver | | | | | 9.00 | |
| Ethylene-propylene Copolymer Viscosity Improver | | | | | | 7.00 |
| Sulfurized Fat | 0.50 | | | | | |
| Reaction Product of an Organo Sulfur Cmpd. with an Epoxide | 0.50 | 0.50 | | | | |
| Sulfurized Olefin | | | | 2.50 | 1.50 | |
| Ester of Dimercapto-thiadiazole | | | 0.17 | | 0.10 | 0.06 |
| Sulfurized Diels-Alder Adduct | | | | | | 0.60 |
| Oil Soluble Phosphorus-Containing Extreme Pressure Agent | | | 1.47 | | | |

TABLE I-continued

| COMPONENTS | A | B | C | D | E | F |
|---|---|---|---|---|---|---|
| Alkylated Arylamine | 0.10 | 0.10 | | | 0.50 | 0.30 |
| Ethoxylated Fatty Amine | 0.09 | 0.09 | | | | |
| Fatty Amide | | | 0.11 | | | 0.10 |
| Fatty Amine | | | | 0.39 | | |
| Silicone Antifoam Agent | 0.042 | 0.042 | 0.066 | | 0.006 | 0.006 |

The products of the various examples, contained in a fully formulated lubricating composition as is described in Table I, were then tested with regard to a Timken "OK" load test as well as a contact pressure test in accordance with ASTM D 2782 with the exception that in the "OK" load test the following procedural differences were made:

1. Test cup and block surfaces are merely "wetted" with test lubricant (approximately 5 drops on block). No test sample is recirculated over the surfaces during the test.
2. Test duration is 5 minutes under load.
3. This procedure is run as an "OK" Load test, determining "OK" Load as in ASTM Test D 2782 except utilizing the following load increments:
   a. "OK" Load is less than or equal to 20 lbs.: Determine "OK" Load to the nearest 1 lb.
   b. "OK" Load is greater than 20 lbs.: Determine "OK" Load using standard load increments as described in ASTM Test D 2782.

The results from testing products of the present invention according to the above tesr procedure are set out in Table II below.

TABLE II

| | | Timken Results | | |
|---|---|---|---|---|
| No. | Sample | # Loading | Unit Press. psi. | Wt %[1] P |
| 1. | Product of Example 2 | 15 | 11,725 | 0.05 |
| 2. | Zinc, 0,0-diisooctyl dithiophosphate | | | 0.05 |
| 3. | Product of Structure V, where R = isooctyl isobutyl amyl mixed alkyl, and $R^2$ = $C_2H_4$— | 20 | 11,950 | 0.05 |
| 4. | Product of Example 3 | 20 | 12,700 | 0.05 |
| 5. | Product of Example 5 | 20 | 11,200 | 0.05 |

[1]Based on the weight of the phosphorous content on the sample.

The invention also includes aqueous compositions characterized by an aqueous phase with at least one amine and/or metal salt of at least one dimer or polymer of the present invention dispersed or dissolved in said aqueous phase. Preferably, this aqueous phase is a continuous aqueous phase although, in some embodiments, the aqueous phase can be a discontinuous phase. These aqueous compositions usually contain at least about 25% by weight water. Such aqueous compositions encompass both concentrates containing about 25% to about 80% by weight, preferably from about 40% to about 65% water; and water-based functional fluids containing generally over about 80% by weight of water. The concentrates generally contain from about 10% to about 90% by weight of at least one of the dimer or polymer additives of the invention. The water-based functional fluids generally contain from about 0.05% to about 15% by weight of the dimer or polymer materials of the invention. The concentrates generally contain less than about 50%, preferably less than about 25%, more preferably less than about 15%, and still more preferably less than about 6% hydrocarbon oil. The water-based functional fluids generally contain less than about 15%, preferably less than about 5%, and more preferably less than about 2% hydrocarbon oil.

These concentrates and water-based functional fluids can optionally include other conventional additives commonly employed in water-based functional fluids. These other additives include surfactants; thickeners; oil-soluble, water-insoluble functional additives such as antiwear agents, extreme pressure agents, dispersants, etc.; and supplemental additives such as corrosion-inhibitors, shear stabilizing agents, bactericides, dyes, water-softeners, odor masking agents, anti-foam agents and the like.

The concentrates are analogous to the water-based functional fluids except except that they contain less water and proportionately more of the other ingredients. The concentrates can be converted to water-based functional fluids by dilution with water. This dilution is usually done by standard mixing techniques. This is often a convenient procedure since the concentrate can be shipped to the point of use before additional water is added. Thus, the cost of shipping a substantial amount of the water in the final water-based functional fluid is saved. Only the water necessary to formulate the concentrate (which is determined primarily be ease of handling and convenience factors), need be shipped.

Generally these water-based functional fluids are made by diluting the concentrates with water, wherein the ratio of water to concentrate is usually in the range of about 80:20 to about 99:1 by weight. As can be seen when dilution is carried out within these ranges, the final water-based functional fluid contains, at most, an insignificant amount of hydrocarbon oil.

In various preferred embodiments of the invention, the water-based functional fluids are in the form of solutions while in other embodiments they are in the form of micelle dispersions or microemulsions which appear to be true solutions. Whether a solution, micelle dispersion or microemulsion is formed is dependent, inter alia, on the particular components employed.

Also included within this invention are methods for preparing aqueous compositions, including both concentrates and water-based functional fluids, containing other conventional additives commonly employed in water-based functional fluids. These methods comprise the steps of:

(1) mixing at least one dimer or polymer additive of the invention with such other conventional additives either simultaneously or sequentially to form a dispersion or solution; optionally (2) combining said dispersion or solution with water to form said aqueous concentrate; and/or (3) diluting said dispersion or solution, or concentrate with water wherein the total amount of water used is in the amount required to provide the desired concentration of the components of the invention and other functional additives in said concentrates or said water-based functional fluids.

These mixing steps are preferably carried out using conventional equipment and generally at room or slightly elevated tempertures, usually below 100° C. and often below 50° C. As noted above, the concentrate can be formed and then shipped to the point of use where it is diluted with water to form the desired water-based functional fluid. In other instances, the finished water-based functional fluid can be formed directly in the same equipment used to form the concentrate or the dispersion or solution.

The surfactants that are useful in the aqueous compositions of the invention can be of the cationic, anionic, nonionic or amphoteric type. Many such surfactants of each type are know to the art. See, for example, McCutcheon's "Emulsifiers & Detergents," 1981, North American Edition, published by McCutcheon Division, MC Publishing Co., Glen Rock, N.J., U.S.A., which is hereby incorporated by reference for its disclosures in this regard.

Among the nonionic surfactant types are the alkylene oxide-treated products, such as ethylene oxide-treated phenols, alcohols, esters, amines and amides. Ethylene oxide/propylene oxide block copolymers are also useful nonionic surfactants. Glycerol esters and sugar esters are also known to be nonionic surfactants. A typical nonionic surfactant class useful with the present invention are the alkylene oxide-treated alkyl phenols such as the ethylene oxide alkyl phenol condensates sold by the Rohm & Haas Company. A specific example of these is Triton X-100 which contains an average of 9–10 ethylene oxide units per molecule, has an HLB value of about 13.5 and a molecular weight of about 628. Many other suitable nonionic surfactants are known; see, for example, the aforementioned McCutcheon's as well as the treatise "Non-Ionic Surfactants" edited by Martin J. Schick, M. Dekker Co., New York, 1967, which is herein incorporated by reference for its disclosures in this regard.

As noted above, cationic, anionic and amphoteric surfactants can also be used. Generally, these are all hydrophilic surfactants. Anionic surfactants contain negatively charged polar groups while cationic surfactants contain positively charged polar groups. Amphoteric dispersants contain both types of polar groups in the same molecule. A general survey of useful surfactants is found in Kirk-Othmer Encyclopedia of Chemical Technology, Second Edition, Volume 19, page 507 et seq. (1969, John Wiley and Son, New York) and the aforementioned compilation published under the name of McCutcheon's. These references are both hereby incorporated by reference for their disclosures relating to cationic, amphoteric and anionic surfactants.

Among the useful anionic surfactant types are the widely known carboxylate soaps, organo sulfates, sulfonates, sulfocarboxylic acids and their salts, and phosphates. Useful cationic surfactants include nitrogen compounds such as amine oxides and the well-known quaternary ammonium salts. Amphoteric surfactants include amino acid-type materials and similar types. Various cationic, anionic and amphoteric dispersants are available from the industry, particularly from such companies as Rohm & Haas and Union Carbide Corporation, both of America. Further information about anionic and cationic surfactants also can be found in the texts "Anionic Surfactants," Parts II and III, edited by W. M. Linfield, published by Marcel Dekker, Inc., New York, 1976, and "Cationic Surfactants," edited by E. Jungermann, Marcel Dekker, Inc., New York, 1976. Both of these references are incorporated by reference for their disclosures in this regard.

These surfactants, when used, are generally employed in effective amounts to aid in the dispersal of the various additivies, particularly the functional additives discussed below, in the concentrates and water-based functional fluids of the invention. Preferably, the concentrates can contain up to about 75% by weight, more preferably from about 10% to about 75% by weight of one or more of these surfactants. The water-based functional fluids can contain up to about 15% by weight, more preferably from about 0.05% to about 15% by weight of one or more of these surfactants.

Often the aqueous compositions of this invention contain at least one thickener for thickening said compositions. Generally, these thickeners can be polysaccharides, synthetic thickening polymers, or mixtures of two or more of these. Among the poly-saccharides that are useful are natural gums such as those disclosed in "Industrial Gums" by Whistler and B. Miller, published by Academic Press, 1959. Disclosures in this book relating to water-soluble thickening natural gums in hereby incorporated by reference. Specific examples of such gums are gum agar, guar gum, gum arabic, algin, dextrans, xanthan gum and the like. Also among the polysaccharides that are useful as thickeners for the aqueous compositions of this invention are cellulose ethers and esters, including hydroxy hydrocarbyl cellulose and hydrocarbylhydroxy cellulose and its salts. Specific examples of such thickeners are hydroxyethyl cellulose and the sodium salt of carboxymethyl cellulose. Mixtures of two or more of any such thickeners are also useful.

It is a general requirement that the thickener used in the aqueous compositions of the present invention be soluble in both cold (10° C.) and hot (about 90° C.) water. This excludes such materials as methyl cellulose which is soluble in cold water but not in hot water. Such hot-water-insoluble materials, however, can be used to perform other functions such as providing lubricity to the aqueous compositions of this invention.

These thickeners can also be synthetic thickening polymers. Many such polymers are known to those of skill in the art. Representative of them are polyacrylates, polyacrylamides, hydrolyzed vinyl esters, water-soluble homo- and interpolymers of acrylamidoalkane sulfonates containing 50 mole percent at least of acryloamido alkane sulfonate and other comonomers such as acrylonitrile, styrene and the like. Poly-n-vinyl pyrrolidones, homo- and copolymers as well as water-soluble salts of styrene, maleic anhydride and isobutylene maleic anhydride copolymers can also be used as thickening agents.

Other useful thickeners are known to those of skill in the art and many can be found in the list in the aforementioned McCutcheon Publication: "Functional Materials," 1976, pp. 135–147, inclusive. The disclosures therein, relative to water-soluble polymeric thickening agents meeting the general requirements set forth above are hereby incorporated by reference.

Preferred thickeners, particularly when the compositions of the invention are required to be stable under high shear applications, are the water-dispersible reaction products formed by reacting at least one hydrocarbyl-substituted succinic acid and/or anhydride represented by the formula

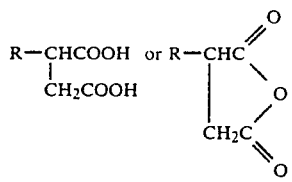

wherein R is a hydrocarbyl group of from about 8 to about 40 carbon atoms, with at least one water-dispersible amine terminated poly(oxyalkylene) or at least one water-dispersible hydroxy-terminated polyoxyalkylene. R preferably has from about 8 to about 30 carbon atoms, more preferably from about 12 to about 24 carbon atoms, still more preferably from about 16 to about 18 carbon atoms. In a preferred embodiment, R is represented by the formula

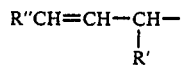

wherein R' and R" are independently hydrogen or straight chain or substantially straight chain hydrocarbyl groups, with the proviso that the total number of carbon atoms in R is within the above-indicated ranges. Preferably R' and R" are alkyl or alkenyl groups. In a particularly advantageous embodiment, R has from about 16 to about 18 carbon atoms, R' is hydrogen or an alkyl group of from 1 to about 7 carbon atoms or an alkenyl group of from 2 to about 7 carbon atoms, and R" is an alkyl or alkenyl group of from about 5 to about 15 carbon atoms.

The water-dispersible amine terminated poly(oxyalkylene)s are preferably alpha omega diamino poly(oxyethylene)s, alpha omega diamino poly(oxypropylene) poly(oxyethylene) poly(oxypropylene)s or alpha omega diamino propylene oxide capped poly(oxyethylene)s. The amine-terminated poly(oxyalkylene) can also be a urea condensate of such alpha omega diamino poly(oxytheylene)s, alpha omega diamino poly(oxypropylene) poly(oxyethylene) poly(oxypropylene)s or alpha omega diamino propylene oxide capped poly(oxyethylene)s. The amine-terminated poly(oxyalkylene) can also be a polyamine (e.g., triamino, tetramino, etc.) polyoxyalkylene provided it is amine-terminated and it is water-dispersible.

Examples of water-dispersible amine-terminated poly(oxyalkylene)s that are useful in accordance with the present invention are disclosed in U.S. Pat. Nos. 3,021,232; 3,108,011; 4,444,566; and RE 31,522. The disclosures of these patents are incorporated herein by reference. Water-dispersible amine terminated poly(oxyalkylene)s that are useful are commercially available from the Texaco Chemical Company under the trade name "Jeffamine."

The water-dispersible hydroxy-terminated polyoxyalkylenes are constituted of block polymers of propylene oxide and ethylene oxide, and a nucleus which is derived from organic compounds containing a plurality of reactive hydrogen atoms. The block polymers are attached to the nucleus at the sites of the reactive hydrogen atoms. Examples of these compounds include the hydroxy-terminated polyoxyalkylenes which are represented by the formula

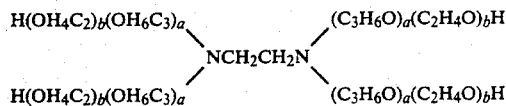

wherein a and b are integers such that the collective molecular weight of the oxypropylene chains range from about 900 to about 25,000, and the collective weight of the oxyethylene chains constitute from about 20% to about 90%, preferably from about 25% to about 55% by weight of the compound. These compounds are commercially available from BASF Wyandotte Corporation under the trade name "Tetronic." Additional examples include the hydroxy-terminated polyoxyalkylenes represented by the formula

wherein y is an integer such that the molecular weight of the oxypropylene chain is at least about 900, and x and z are integers such that the collective weight of the oxyethylene chains constitute from about 20% to about 90% by weight of the compound. These compounds preferably have a molecular weight in the range of about 1,100 to about 14,000. These compounds are commercially available from BASF Wyandotte Corporation under the trade name "Pluronic." Useful hydroxy-terminated polyoxyalkylenes are disclosed in U.S. Pat. Nos. 2,674,619 and 2,979,528, which are incorporated herein by reference.

The reaction between the carboxylic agent and the amine- or hydroxy-terminated polyoxyalkylene can be carried out at a temperature ranging from the highest of the melt temperatures of the reaction components up to the lowest of the decomposition temperatures of the reaction components or products. Generally, the reaction is carried out at a temperature in the range of about 60° C. to about 160° C., preferably about 120° C. to about 160° C. The ratio of equivalents of carboxylic agent to polyoxyalkylene preferably ranges from about 0.1:1 to about 8:1, preferably about 1:1 to about 4:1, and advantageously about 2:1. The weight of an equivalent of the carboxylic agent can be determined by dividing its molecular weight by the number of carboxylic functions present. The weight of an equivalent of the amine-terminated polyoxyalkylene can be determined by dividing its molecular weight by the number of terminal amine groups present. The weight of an equivalent of the amine-terminated polyoxyalkylene can be determined by dividing its molecular weight by the number of terminal amine groups present. The number of terminal amine and hydroxyl groups can usually be determined from the structural formula of the polyoxyalkylene or empirically through well-known procedures. The amine/acids and ester/acids formed by the reaction of the carboxylic agent and amine-terminated or hydroxy-terminated polyoxyalkylene can be neutralized with, for example, one or more alkali metals, one or more amines, or a mixture thereof, and thus converted to amide/salts or ester/salts, respectively. Additionally, if these amide/acids or ester/acids are added to concentrates or functional fluids containing alkali metals or amines, amide/salts or ester/salts usually form, in situ.

South African Pat. No. 85/0978 is incorporated herein by reference for its teachings with respect to the use of hydrocarbyl-substituted succinic acid or anhydride/hydroxy-terminated poly(oxyalkylene) reaction products as thickeners for aqueous compositions.

When the thickener is formed using an amine-terminated poly(oxyalkylene), the thickening characteristics of said thickener can be enhanced by combining it with at least one surfactant. Any of the surfactants identified above under the subtitle "Surfactants" can be used in this regard. When such surfactants are used, the weight ratio of thickener to surfactant is generally in the range of from about 1:5 to about 5:1, preferably from about 1:1 to about 3:1.

Typically, the thickener is present in a thickening amount in the aqueous compositions of this invention. When used, the thickener is preferably present at a level of up to about 70% by weight, preferably from about 20% to about 50% by weight of the concentrates of the invention. The thickener is preferably present at a level in the range of from about 1.5% to about 10% by weight, preferably from about 3% to about 6% by weight of the functional fluids of the invention.

The functional additives that can be used in the aqueous systems are typically oil-soluble, water-insoluble additives which function in conventional oil-based systems as extreme pressure agents, antiwear agents, load-carrying agents, dispersants, friction modifiers, lubricity agents, etc. They can also function as anti-slip agents, film formers and friction modifiers. As is well known, such additives can function in two or more of the above-mentioned ways; for example, extreme pressure agents often function as load-carrying agents.

The term "oil-soluble, water-insoluble functional additive" refers to a functional additive which is not soluble in water above a level of about 1 gram per 100 milliliters of water at 25° C., but is soluble in mineral oil to the extent of at least 1 gram per liter at 25° C.

These functional additives can also include certain solid lubricants such as graphite, molybdenum disulfide and polytetrafluoroethylene and related solid polymers.

These functional additives can also include frictional polymer formers. Briefly, these are potential polymer forming materials which are dispersed in a liquid carrier at low concentration and which polymerize at rubbing or contacting surfaces to form protective polymeric films on the surfaces. The polymerizations are believed to result from the heat generated by the rubbing and, possibly, from catalytic and/or chemical action of the freshly exposed surface. A specific example of such materials is dilinoleic acid and ethylene glycol combinations which can form a polyester frictional polymer film. These materials are known to the art and descriptions of them are found, for example, in the journal "Wear," Volume 26, pages 369–392, and West German Published Patent Application 2,339,065. These disclosures are hereby incorporated by reference for their discussions of frictional polymer formers.

Typically these functional additives are known metal or amine salts of organo sulfur, phosphorus, boron or carboxylic acids which are the same as or of the same type as used in oil-based fluids. Typically such salts are of carboxylic acids of 1 to 22 carbon atoms including both aromatic and aliphatic acids; sulfur acids such as alkyl and aromatic sulfonic acids and the like; phosphorus acids such as phosphoric acid, phosphorus acid, phosphinic acid, acid phosphate esters and analogous sulfur homologs such as the thiophosphoric and dithiophosphoric acid and related acid esters; boron acids include boric acid, acid borates and the like. Useful functional additives also include metal dithiocarbamates such as molybdenum and antimony dithiocarbamates; as well as dibutyl tin sulfide, tributyl tin oxide, phosphates and phosphites; borate amine salts, chlorinated waxes; trialkyl tin oxide, molybdenum phosphates, and chlorinated waxes.

Many such functional additives are known to the art. For example, descriptions of additives useful in conventional oil-based systems and in the aqueous systems of this invention are found in "Advances in Petroleum Chemistry and Refining," Volume 8, edited by John J. McKetta, Interscience Publishers, New York, 1963, pages 31-38 inclusive; Kirk-Othmer "Encyclopedia of chemical Technology," Volume 12, Second Edition, Interscience Publishers, New York, 1967, page 575 et seq.; "Lubricant Additives" by M. W. Ranney, Noyes Data Corporation, Park Ridge, N.J., U.S.A., 1973; and "Lubricant Additives" by C. V. Smalheer and R. K. Smith, The Lezius-Hiles Co., Cleveland, Ohio, U.S.A. These references are hereby incorporated by reference for their disclosures of functional additives useful in the compositions of this invention.

In certain of the typical aqueous compositions of the invention, the functional additive is a sulfur or chlorosulfur extreme pressure agent, known to be useful in oil-base systems. Such materials include chlorinated aliphatic hydrocarbons, such as chlorinated wax; organic sulfides and polysulfides, such as benzyl-disulfide, bis-(chlorobenzyl)disulfide, dibutyl tetrasulfide, sulfurized sperm oil, sulfurized methyl ester of oleic acid, sulfurized alkylphenol, sulfurized dipentene, sulfurized terpene, and sulfurized Diels-Alder adducts; phosphosulfurized hydrocarbons, such as the reaction product of phosphorus sulfide with turpentine or methyl oleate, phosphorus ester such as the dihydrocarbon and trihydrocarbon phosphites, i.e., dibutyl phosphite, diheptyl phosphite, dicyclohexyl phosphite, pentylphenyl phosphite, dipentylphenyl phosphite, tridecyl phosphite, distearyl phosphite and polypropylene substituted phenol phosphite; metal thiocarbamates, such as zinc dioctyldithiocarbamate and barium heptylphenol dithiocarbamate; and Group II metal salts of a phosphorodithioic acid, such as zinc dicyclohexyl phosphorodithioate.

The functional additive can also be a film former such as a synthetic or natural latex or emulsion thereof in water. Such latexes include natural rubber latexes and polystyrene butadienes synthetic latex.

The functional additive can also be an anti-chatter or anti-squawk agent. Examples of the former are the amide metal dithiophosphate combinations such as disclosed in West German Pat. No. 1,109,302; amine salt-azomethane combinations such as disclosed in British Patent Specification No. 893,977; or amine dithiophosphate such as disclosed in U.S. Pat. No. 3,002,014. Examples of anti-squawk agents are N-acyl-sarcosines and derivatives thereof such as disclosed in U.S. Pat. Nos. 3,156,652 and 3,156,653; sulfurized fatty acids and esters thereof such as disclosed in U.S. Pat. Nos. 2,913,415 and 2,982,734; and esters of dimerized fatty acids such as disclosed in U.S. Pat. No. 3,039,967. The above-cited patents are incorporated herein by reference for their disclosure as pertinent to anti-chatter and anti-squawk agents useful as a functional additive in the aqueous systems of the present invention.

Specific examples of functional additives useful in the aqueous systems of this invention include the following commercially available products.

TABLE I

| Functional Additive Trade Name | Chemical Description | Supplier |
|---|---|---|
| Anglamol 32 | Chlorosulfurized hydrocarbon | Lubrizol[1] |
| Anglamol 75 | Zinc dialkyl phosphate | Lubrizol[1] |
| Molyvan L | A thiaphosphomolybdate | Vanderbilt[2] |
| Lubrizol-5315 | Sulfurized cyclic carboxylate ester | Lubrizol[1] |
| Emcol TS 230 | Acid phosphate ester | Witco[3] |

[1]The Lubrizol Corporation, Wickliffe, Ohio, U.S.A.
[2]R. T. Vanderbilt Company, Inc., New York, New York, U.S.A.
[3]Witco Chemical Corp., Organics Division, Houston, Texas, U.S.A.

Mixtures of two or more of any of the afore-described functional additives can also be used.

Typically, a functionally effective amount of the functional additive is present in the aqueous compositions of this invention.

The term "functionality effective amount" refers to a sufficient quantity of an additive to impart desired properties intended by the addition of said additive. For example, if an additive is a rust-inhibitor, a functionally effective amount of said rust-inhibitor would be an amount sufficient to increase the rust-inhibiting characteristics of the composition to which it is added. Similarly, if the additive is an antiwear agent, a functionally effective amount of said antiwear agent would be a sufficient quantity of the antiwear agent to improve the antiwear characteristics of the composition to which it is added.

The aqueous systems of this invention often contain at least one inhibitor for corrosion of metals. These inhibitors can prevent corrosion of either ferrous or non-ferrous metals (e.g., copper, bronze, brass, titanium, aluminum and the like) or both. The inhibitor can be organic or inorganic in nature. Usually it is sufficiently soluble in water to provide a satisfactory inhibiting action though it can function as a corrosion-inhibitor without dissolving in water, it need not be water-soluble. Many suitable inorganic inhibitors useful in the aqueous systems of the present invention are known to those skilled in the art. Included are those described in "Protective Coatings for Metals" by Burns and Bradley, Reinhold Publishing Corporation, Second Edition, Chapter 13, pages 596-605. This disclosure relative to inhibitors are hereby incorporated by reference. Specific examples of useful inorganic inhibitors include alkali metal nitrites, sodium di- and tripolyphosphate, potassium and dipotassium phosphate, alkali metal borate and mixtures of the same. Many suitable organic inhibitors are known to those of skill in the art. Specific examples include hydrocarbyl amine and hydroxy-substituted hydrocarbyl amine neutralized acid compund, such as neutralized phosphates and hydrocarbyl phosphate esters, neutralized fatty acids (e.g., those having about 8 to about 22 carbon atoms), neutralized aromatic carboxylic acids (e.g., 4-tertiarybutyl benzoic acid), neutralized naphthenic acids and neutralized hydrocarbyl sulfonates. Mixed salt esters of alkylated succinimides are also useful. Particularly useful amines include the alkanol amines such as ethanol amine, diethanolamine. Mixtures of two or more of any of the afore-described corrosion-inhibitors can also be used. The corrosion-inhibitor is usually present in concentrations in which they are effective in inhibiting corrosion of metals with which the aqueous composition comes in contact.

Certain of the aqueous systems of the present invention (particularly those that are used in cutting or shaping of metal) can also contain at least one polyol with inverse solubility in water. Such polyols are those that become less soluble as the temperature of the water increases. They thus can function as surface lubricity agents during cutting or working operations since, as the liquid is heated as a result of friction between a metal workpiece and work tool, the polyol of inverse solubility "plates out" on the surface of the workpiece, thus improving its lubricity characteristics.

The aqueous systems of the present invention can also include at least one bactericide. Such bactericides are well known to those of skill in the art and specific examples can be found in the afore-mentioned McCutcheon publication "Functional Materials" under the heading "Antimicrobials" on pages 9–20 thereof. This disclosure is hereby incorporated by reference as it relates to suitable bactericides for use in the aqueous compositions or systems of this invention. Generally, these bactericides are water-soluble, at least to the extent to allow them to function as bactericides.

The aqueous systems of the present invention can also include such other materials as dyes, e.g., an acid green dye; water softeners, e.g., ethylene diamine tetraacetate sodium salt or nitrilo triacetic acid; odor masking agents, e.g., citronella, oil of lemon, and the like; and anti-foamants, such as the well-known silicone anti-foamant agents.

The aqueous systems of this invention may also include an antifreeze additive where it is desired to use the composition at a low temperature. Materials such as ethylene glycol and analogous polyoxyalkylene polyols can be used as antifreeze agents. Clearly, the amount used will depend on the degree of antifreeze protection desired and will be known to those of ordinary skill in the art.

It should also be noted that many of the ingredients described above for use in making the aqueous systems of this invention are industrial products which exhibit or confer more than one property on such aqueous compositions. Thus, a single ingredient can provide several functions thereby eliminating or reducing the need for some other additional ingredient. Thus, for example, and extreme pressure agent such as tributyl tin oxide can also function as a bactericide.

While the invention has been described and illustrated with reference to certain preferred embodiments thereof, those skilled in the art will appreciate that various changes, modifications and substitutions can be made therein without departing from the spirit of the invention. For example, different concentration ranges other than the preferred ranges set forth hereinabove may be applicable as a consequence of variations in the oil base stock or the type of engine or the like. It is intended, therefore, that the invetnion be limited only by the scope of the claims which follow.

What is claimed is:

1. A dimer ester of the formula:

A—T—A  (I)

wherein A is

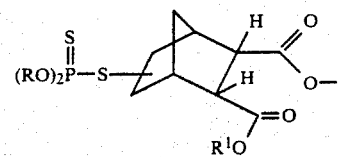

where R is alky, aryl or aralkyl and $R^1$ is, independently hydrogen or hydrocarbyl and T is hydrocarbyl.

2. The dimer ester according to claim 1 wherein R is alkylene of 1 to about 6 carbon atoms, and $R^1$ is alkyl of 2 to about 12 carbon atoms.

3. The dimer ester according to claim 2 wherein R is ethylene, and $R^1$ is alkyl of 2 to about ∂carbon atoms.

4. A polyester of the formula:

wherein X and Y are terminal groups of the polymer and are, independently, hydrogen, alkyl, aryl, aralkyl, hydroxy, alkoxy, carboalkoxy, aryloxy, dialkylamino, diarylamino, alkylthio or arylthio; p is 3 to about 30; r is 0 to about 30 and the sum of p+r ranges from 3 to about 40; D is

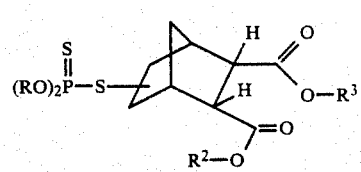

wherein R is alkyl, aryl or aralkyl and $R^2$ and $R^3$ are hydrocarbyl or a bond to other repeating units; and E is

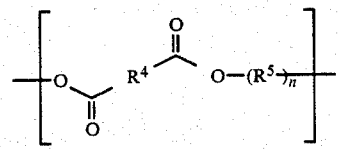

wherein $R^4$ and $R^5$ are the same or different and are hydrocarbyl which includes branched hydrocarbyl groups containing reactive functionalities thereof, and n is 0 or 1.

5. The polyester according to claim 4 wherein p is 4 to 10, r is 0, and $R^3$ alkylene of 1 to about 6 carbon atoms.

6. The polyester according to claim 5 wherein $R^3$ is ethylene.

7. The polyester according to claim 4 wherein p is 4 to 10, r is 3 to 10 and the sum of p+r ranges from 7 to 12; $R^3$ is alkylene of 1 to about 6 carbon atoms; $R^4$ and $R^5$ are alkylated succinic radicals wherein the alkyl group contains abour 8 to about 200 carbon atoms.

8. A diester prepared from reactants comprising:
(A) 5-norbornene-2,3-dicarboxylic anhydrides;
(B) 0,0-dialkyldithiophosphoric acid containing 1 to about 30 carbon atoms; and
(C) a polyol; wherein the adduct of (A) and (B) is condensed with polyol (C) in such a ratio and under conditions such that the product is a dimeric ester of the formula: A-T-A wherein A is

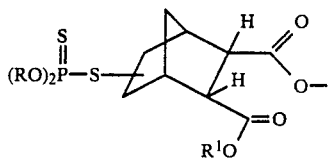

where R is alkyl, aryl or aralkyl and $R^1$ is, independently, hydrogen or hydrocarbyl and T is hydrocarbyl.

9. The dimer ester according to claim 8 wherein said polyol is an alkylene glycol.

10. The dimer ester according to claim 9 wherein said alkylene glycol is ethylene glycol.

11. A polyester prepared from reactants comprising:
(A) 5-norbornene-2,3-dicarboxylic anhydrides;
(B) 0,0-dialkyldithiophosphoric acid containing 1 to about 30 carbon atoms; and
(C) a polyol; wherein the reaction is carried out such that equivalent ratios of OH:C=O are used, the reaction is carried out to the point of complete removal of water and the polyester prepared has a molecular weight of about 1000 to about 10,000.

12. The polyester according to claim 11 wherein said polyol is an alkylene glycol.

13. The polyester according to claim 12 wherein said alkylene glycol is ethylene glycol.

14. The polyester according to claim 11 wherein said polyester is further prepared from an additional polycarboxylic acid or derivative thereof.

15. The polyester according to claim 14 wherein said additional polycarboxylic acid is an alkylated succinic acid or derivative thereof wherein said alkyl group contains about 8 to about 200 carbon atoms.

16. A lubricating composition comprising a major amount of a lubricating oil of lubricating viscosity and a minor effective amount of at least one dimer ester and/or polyester of any one of claims 1 to 15.

17. A concentrate for formulating a lubricant composition comprising from about 1% to about 99% by weight of at least one dimer ester and/or polyester of any one of claims 1 to 15 and a normally liquid, substantially inert organic solvent/diluent.

18. An additive for formulating lubricant compositions comprising at least one dimer ester or polyesters of any one of claims 1 to 15.

19. A method for improving the load bearing properties and dispersancy of lubricant compositions by admixing a minor effective amount of at least one dimer ester and/or polyester of any one of claims 1 to 15 with a major amount of a lubricating oil of lubricating viscosity.

20. A grease composition comprising a minor effective amount of at least one dimer ester or polyester of any one of claims 1 to 15.

21. An aqueous functional fluid comprising a minor effective amount of at least one dimer ester or polyester of any one of claims 1 to 15.

* * * * *